June 11, 1957 R. G. CREMER Plant Pat. 1,607
ROSE PLANT
Filed Jan. 10, 1956
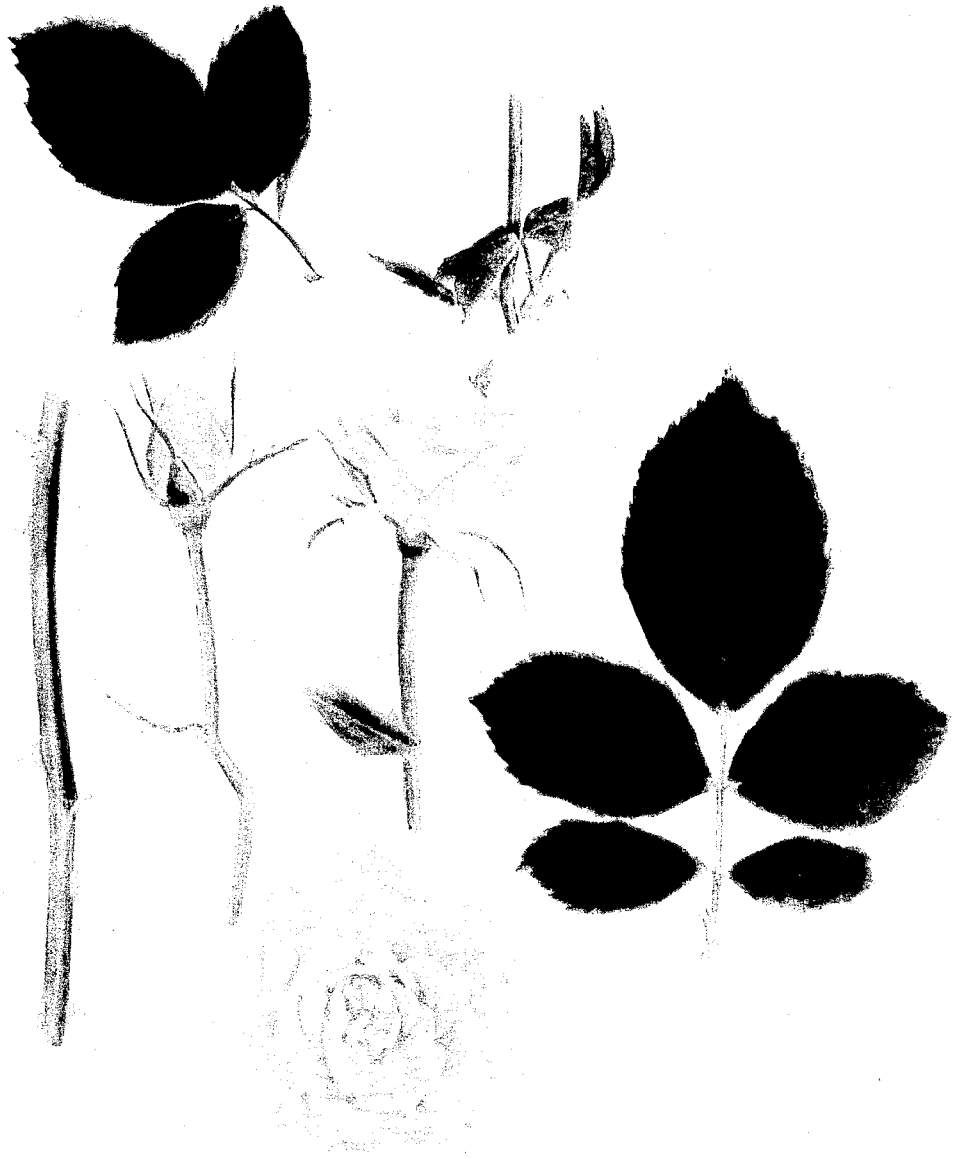
INVENTOR
Rosella Grace Cremer
By Orville M. Kile
Plant Patent Agent United States Patent Office Plant Pat. 1,607
Patented June 11, 1957

1,607

ROSE PLANT

Rosella Grace Cremer, Hanover, Pa.

Application January 10, 1956, Serial No. 558,394

1 Claim. (Cl. 47—61)

My present discovery relates to a new variety of rose plant of the polyantha type, the color of its flowers being one of its distinguishing features. It originated in my greenhouses at Hanover, Pennsylvania, as a sport of the variety Garnette (unpatented). I have asexually reproduced the new variety at the same location by means of cuttings, and its characteristics appear to be firmly fixed.

This new sport is similar to its parent in many respects, particularly as to growth habits, and also somewhat resembles the Garnette sport "Pink Garnette" (Plant Patent No. 1,120).

The accompanying illustrations are hand-colored photographs of three specimens of the bloom of my new variety in various stages of opening, together with portions of stem and foliage (both mature and new). These are in as nearly their true colors as it was possible for the artist to make them, but some allowance must be made for variations.

In the following detailed description of the plant and flower, plate numbers refer to Ridgway's Color Standards and Nomenclature. Other color names refer to the ordinary dictionary meaning of the term.

*The plant*

Growth: Bushy; very vigorous, attaining a height of 5 to 6 feet; breaks freely.

Blooming habit: Continuous and very prolific bloomer.

Borne: Singly on stems of approximately 12 to 14 inches in length, which in turn are usually in irregular clusters.

Stems:

*Color.*—Between Lettuce Green and Spinach Green (Plate V).

*Strength.*—Slender but very strong.

*Type.*—Zigzagged type, with short internodes.

*Thorns.*—Irregularly spaced; narrow-based; downward-pointing; red-tinged.

Foliage:

*Type.*—Usually 3 to 5 leaflets; occasionally 7.

*Quantity.*—Abundant; close to flower because of short peduncle.

*Size.*—Medium. Terminal leaflet measures 1½ to 2¼ inches long and 1¼ to 1½ inches wide.

*Shape.*—Broadly ovate, with rounded base and acute apex.

*Texture.*—Leathery.

*Color.*—Typical mature foliage is between Forest Green and Elm Green (Plate XVII) on upper surface, with under surface approximately Bice Green (Plate XXXI). New foliage is from Brazil Red to Garnet Brown (Plate I).

*Rachis.*—Slender; grooved above; mostly smooth on under surface.

*Stipules.*—Narrow; clinging except for long points.

*Disease resistant.*—Where tested in my gardens at Hanover under usual growing conditions, this variety is very resistant to diseases, having had no blackspot and very little mildew.

*Flower*

Bud:

*Size.*—Small; approximately ¾ inch long.

*Color.*—When color first shows, it is approximately Carmine (Plate I). Later the bud is approximately Tyrian Rose (Plate XII).

*Shape.*—Conical to ovoid.

*Sepals.*—Branched, usually two are slightly folliaceous.

*Calyx.*—Pearshaped; small; smooth.

*Peduncle.*—Short; slender but strong, holding bloom erect. Same color as stems.

Bloom:

*Size.*—Small to medium. Averages 1½ to 1¾ inches in diameter.

*Form.*—Very full. At first almost straight across top. Typical opening flower has an upstanding cupped center which forms a rosette, while several outer rows of petals are slightly reflexed and imbricated. Fully opened flower is cup-shaped.

*Petalage.*—Very double, petals numbering around 35 to 40 as an average in the fall and winter months.

*Longevity.*—Very long-lasting; in ordinary room temperatures it remains in good condition for at least ten days.

*Fragrance.*—Moderate amount of usual rose fragrance.

*Color.*—Color darkens as flower opens, with the exception that the white aiglet of the petals is more evident as the opening progresses. Color of the open flower is not found in Ridgway's Color Standards, although it is in the range of Plate XII. The inner surface of the petals of the open flower is darker than Tyrian yet is not purplish. Sometimes the edges of the outer petals are as light as Rose Color, although at other times the flower appears to have a uniform color which is darker than Tyrian. Outer surface of petals is somewhat lighter.

Petals:

*Size.*—Outer petals are ¾ to ⅞ inch wide and slightly longer. Inner petals are much shorter and narrower.

*Shape.*—Broadly obovate. Slightly cupped and often appear to be folded in the center. Edge smooth except for extremely small point at tip. However, a slight reflexing of the petals sometimes gives a more pointed effect.

*Arrangement.*—Imbricated.

*Appearance.*—Slightly velvety on upper surface; under surface silky.

*Texture.*—Substantial; moderately heavy.

Reproductive organs:

*Pistils.*—Many; very tightly bunched in center of flower. Styles—short and reddish-tinged. Stigmas—small; light yellow, approximately Baryta

*Stamens.*—Few or none. Anthers—approximately Buff Yellow (Plate IV). Filaments—white to greenish-white.

*Comparison*

The variety most like my new variety is Pink Garnette (Pl. Pat. 1,120). Plants and flowers of the two varieties grown under similar conditions and observed at the same time, show the principal differences as follows:

1. Although the color of the buds of the two varieties is very much alike, the open flower of my variety is much darker and more velvety in appearance.

2. The size of the flowers of my variety is somewhat smaller—average being 1½ to 1¾ inches as compared with an average of 2¼ to 2½ inches for Pink Garnette.

3. The petals of my variety have more of a tendency to pointedness at the tip, and the Pink Garnette petals have more of a tendency to wavy edges.

4. Serrations of the leaves of my variety do not appear to be as deep as those of Pink Garnette.

5. New foliage on my variety is not quite so dark in color.

6. The plant of my variety grows taller than that of Pink Garnette.

Having thus disclosed my discovery, I claim:

The new and improved variety of polyantha rose plant, with combination of features substantially as herein shown and described, characterized particularly by its tall, bushy growth; its prolific production of flowers; and its flowers of small to medium size, velvety appearance, and distinctive "darker than Tyrian" color.

No references cited.